United States Patent [19]
Eichelberger et al.

[11] Patent Number: 5,842,993
[45] Date of Patent: Dec. 1, 1998

[54] NAVIGABLE ULTRASONIC IMAGING PROBE ASSEMBLY

[75] Inventors: Eric Evan Eichelberger, Tualatin; Arthur Glen Buck, Sherwood, both of Oreg.

[73] Assignee: The Whitaker Corporation, Wilmington, Del.

[21] Appl. No.: 987,941

[22] Filed: Dec. 10, 1997

[51] Int. Cl.⁶ ........................................................ A61B 8/00

[52] U.S. Cl. ............................................................ 600/462

[58] Field of Search .................................... 600/443, 444, 600/445, 446, 459, 461, 462, 463, 466, 467

[56] References Cited

U.S. PATENT DOCUMENTS

| | | | |
|---|---|---|---|
| 3,901,574 | 8/1975 | Paullus et al. | 339/90 |
| 5,158,086 | 10/1992 | Brown et al. | 128/662 |
| 5,413,107 | 5/1995 | Oakley et al. | 128/662 |
| 5,445,155 | 8/1995 | Sieben | 600/443 |
| 5,592,942 | 1/1997 | Webler et al. | 600/445 |
| 5,715,825 | 2/1998 | Crowley | 1/1 |

*Primary Examiner*—George Manuel
*Attorney, Agent, or Firm*—Gerald K. Kita

[57] ABSTRACT

An ultrasound imaging probe assembly (3) has articulation control cables (4) and a rotating cable (6) enclosed by sheaths (16) in a signal transmitting cable (40), and the sheaths (16) extend inside a portion of the cable (40) to contain insulated wires (51) that supply power to reversible motors (10, 10a) that drive the cables (4 and 6).

6 Claims, 4 Drawing Sheets

NAVIGABLE ULTRASONIC IMAGING PROBE ASSEMBLY

FIELD OF THE INVENTION

The invention relates to a navigable probe assembly with a motor operated drive mechanism.

BACKGROUND OF THE INVENTION

A navigable probe may comprise, for example, a gastroscope and transesophagel type medical ultrasound imaging probe as described in U.S. Pat. No. 5,445,154. The probe contains an ultrasound imaging transducer at the end of a flexible cable. The probe is used for medical diagnosis, for example, by inserting the probe inside a body cavity of a patient, and acquiring an ultrasound image by using an ultrasonic transducer. A tip of the probe is adapted to flex to a curved shape in different directions of flexure. Individual torque and articulation control cables extend through the probe.

By pulling on individual cables, the probe tip can be flexed or extended to a curved shape, thus, to traverse the probe along bends of a body cavity, and to point the imaging transducer in different directions. The probe cable may contain a torque control cable capable of transmitting a twisting force or twisting motion through the probe and its articulating section while the section is flexed into a curved shape. The torque control cable may be used for transducer rotation to allow imaging along different planes. Adjusting the probe to a curved shape and rotating the torque control cable, currently requires careful hand operation, and hand operation is required to start and stop the movement of the probe to avoid injuring a patient with the probe.

SUMMARY OF THE INVENTION

A navigable probe assembly with an ultrasound imaging transducer connected to signal transmitting conductors of a cable assembly, has a reversible motor and a reversible drive mechanism connected to reciprocating articulation control cables for bending the probe assembly, and a reversible motor connected to insulated wires of the cable assembly.

A navigable probe assembly comprises, reciprocating articulation control cables for bending a portion of the probe assembly, a reversible motor to reciprocate the cables, and a cable assembly having signal transmitting cables connected to an ultrasound imaging transducer on the probe assembly. Insulated wires extend along a second portion of the cable assembly and connect with the motor to supply power to the motor. The control cables are within sheaths in a first portion of the cable assembly. The sheaths in a second portion of the cable assembly contain the insulated wires.

A navigable probe assembly has a housing containing a reversible motor and a reversible drive mechanism, and a cable assembly extends through the housing, a first portion of the cable assembly having reciprocating articulation control cables for bending a bendable portion of the probe assembly, a second portion of the cable assembly having insulated wires connected to the motor for supplying power to the motor, and the cable assembly being contained in the housing, with said first portion of said cable assembly extending from a first portion of said housing, and said second portion of said cable assembly extending from a second portion of said housing.

BRIEF DESCRIPTION OF THE DRAWINGS

Embodiments of the invention will now be described by way of example with reference to the accompanying drawings, according to which:

FIG. 4a is a schematic view of insulated wires electrically connected to reversible switches and reversible motors and one insulated wire referenced to ground or earth electrical potential.

DETAILED DESCRIPTION

Figure 1:
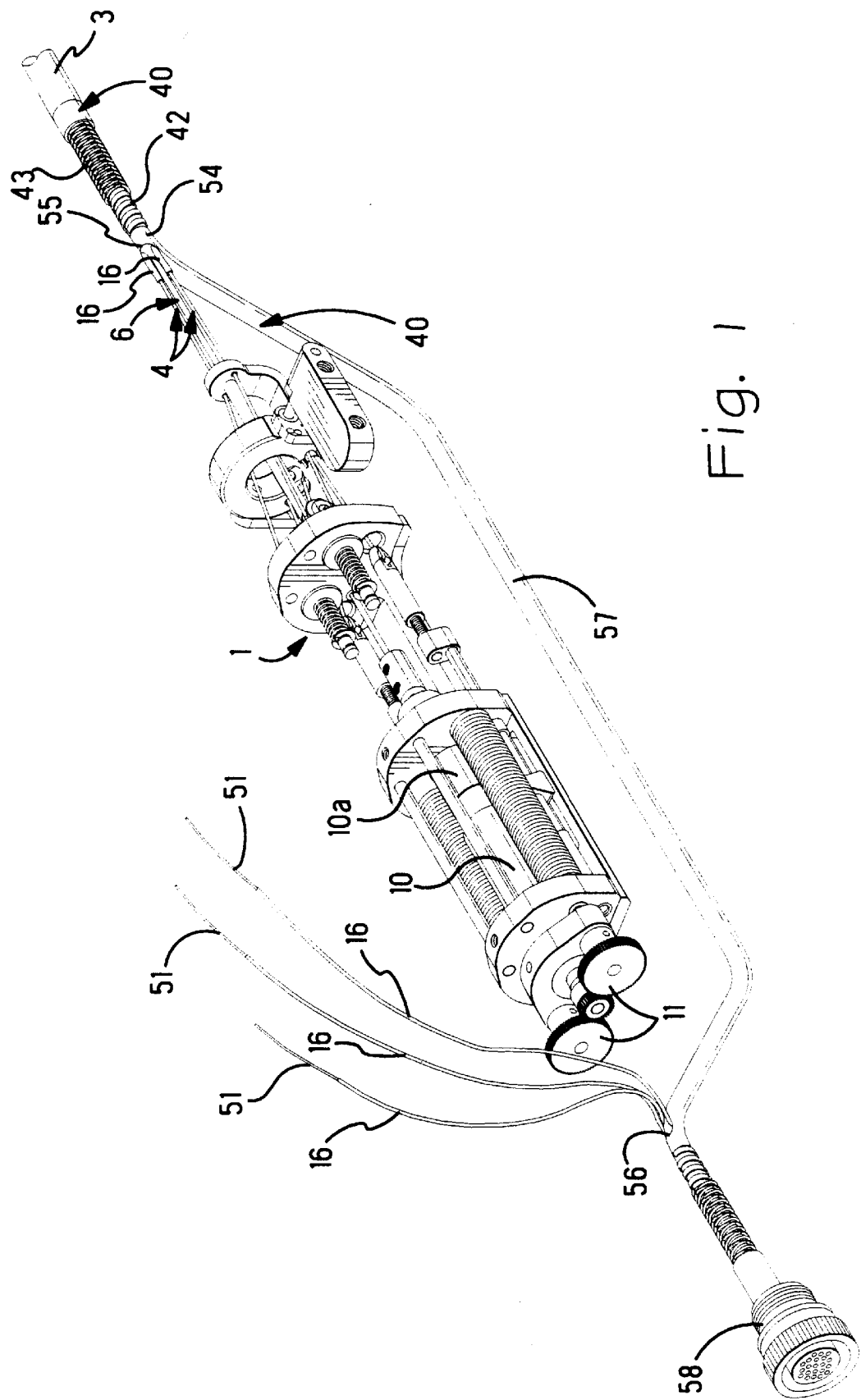
FIG. 1 is a schematic view of a navigable ultrasonic imaging probe assembly.
Figure 2:
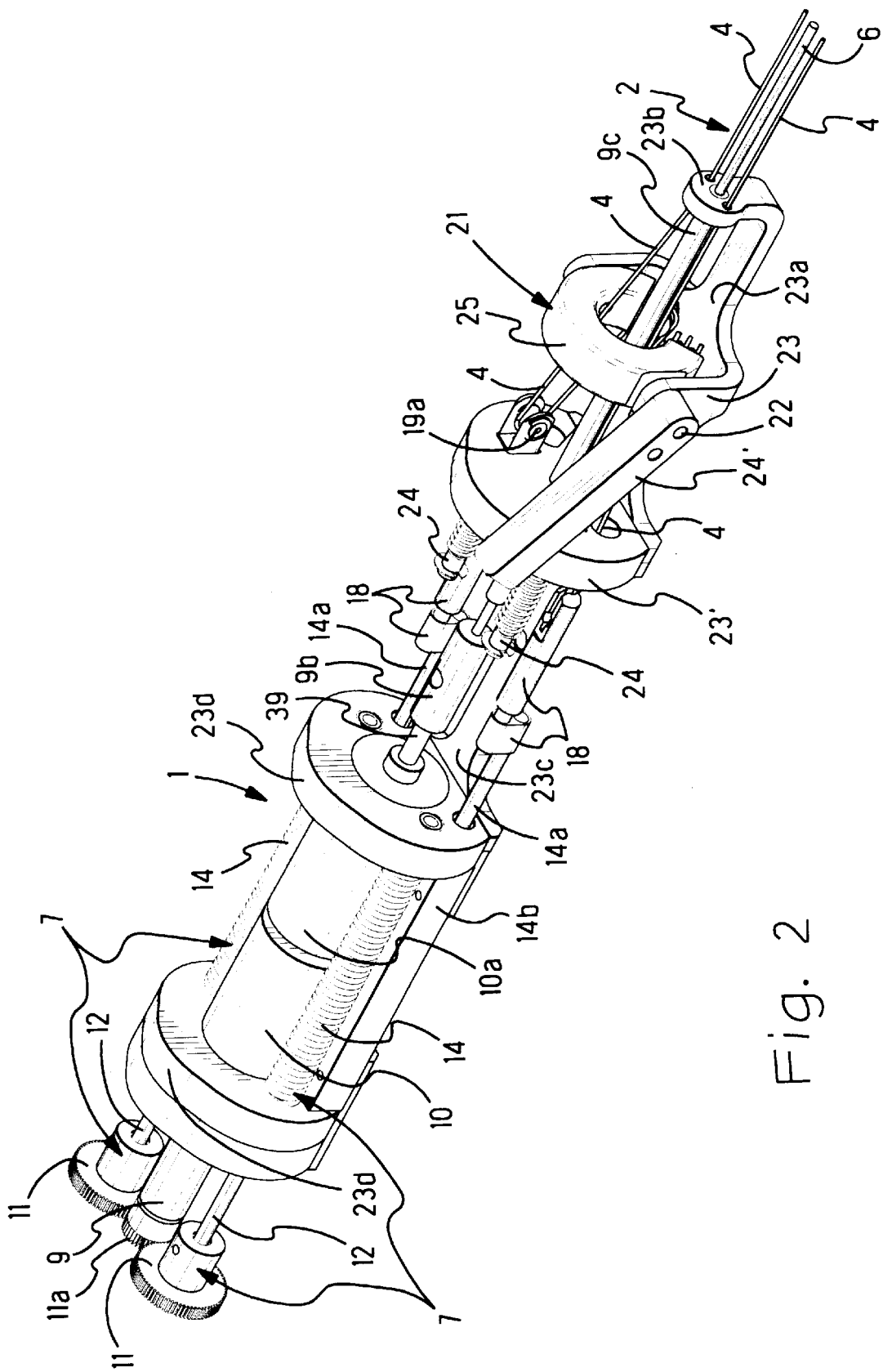
FIG. 2 is a view similar to FIG. 1, of a portion of the navigable probe assembly as shown in FIG. 1.

With reference to FIGS. 2, a motor control apparatus (1) for a navigable probe assembly, for example, a medical ultrasound imaging probe assembly, of an ultrasound imaging transducer, not shown, is comprised of one or more articulation control cables (4) extending along a flexible elongated bendable probe assembly (3), FIG. 1, to flex the bendable probe assembly (3) to a curved configuration in various degrees of flexure by pulling on one or more articulation control cables (4). Additional cables (4) may extend along the bendable probe assembly (3) to flex the bendable probe assembly (3) in various degrees of flexure, and in one or more additional directions of flexure, by applying tension to an alternate control cable (4, 4), by alternately pulling on individual cables (4), to effect the articulation of the tip of the probe assembly (3).

Figure 3:
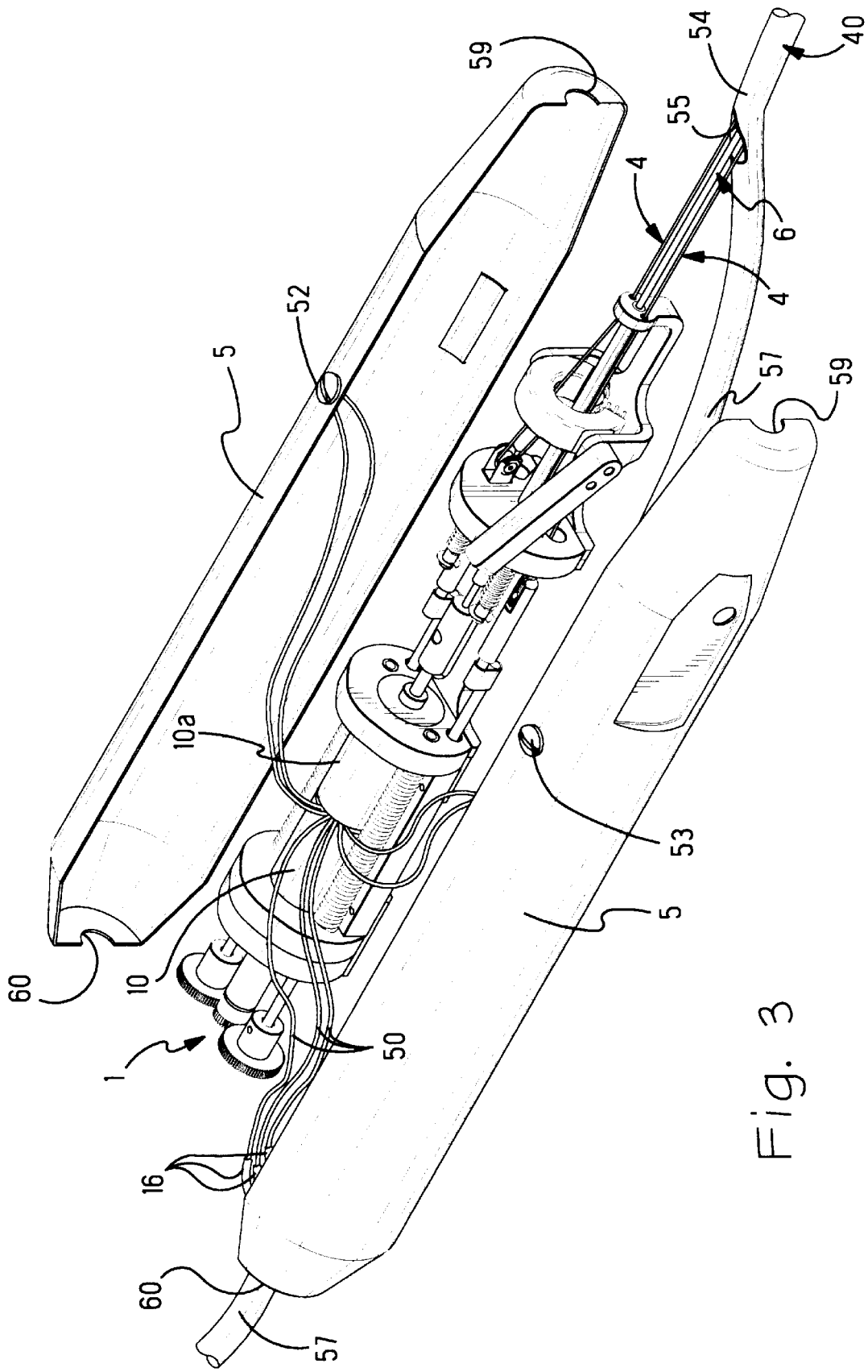
FIG. 3 is a view similar to FIG. 2, illustrating a cable assembly and a housing combined with the portion of the navigable probe assembly as shown n FIG. 2.

A medical ultrasound imaging probe assembly is further comprised of the elongated bendable probe assembly (3) attached to a housing (5), FIG. 3. Details of the bendable probe assembly (3) are described in U.S. Pat. No. 5,445,154. Individual articulation control cables (4, 4) of each corresponding cable pair (2) are radially spaced from a rotating torque control cable (6), also called, a central control cable (6), extending to a known ultrasound imaging transducer, not shown, within the articulating end of the bendable probe assembly (3). With reference to FIG. 3, the motor control apparatus (1) is mounted on a housing (5), and is adapted to be operated by digits on one hand of a human operator that grasps the housing (5). The motor control apparatus (1), is in an interior of the housing (5) to flex the bendable probe assembly (3), by alternately pulling on individual articulation control cables (4, 4) of the corresponding cable pair (2). At least one articulation control cable (4) is required to flex the bendable probe assembly (3) to various degrees of flexure. Thus, one or more articulation control cables (4) are intended to be actuated by the motor control apparatus (1).

With reference to FIG. 2, the motor control apparatus (1) further comprises, a reversible articulation control motor (10) driving a reversible drive mechanism (7) connected to the corresponding articulation control cables (4, 4). A narrow configuration is provided to hold and manipulate the motor control apparatus (1) with a single hand of a person. Referencing FIG. 2, for example, the motor control apparatus (1) is parallel with longitudinal axes of the parallel articulation control cables (4, 4). The articulation control motor (10) is in tandem alignment with the axes of the close together, articulation control cables (4, 4). The articulation control motor (10) is a reversible electric torque motor, with its longitudinal axis being parallel with longitudinal axes of the articulation control cables (4, 4), where the articulation control cables (4, 4) extend forwardly of the motor control apparatus (1).

A relatively slender dimension of the articulation control motor (10) is oriented transversely of the longitudinal axes of the articulation control cables (4, 4) to result in a slender lengthwise housing (5) that is easily grasped by a human operator.

The articulation control motor (10) is designed to provide a selected, maximum torque output, as a safety feature, to restrict the drive mechanism (7) from farther movement by stopping farther rotation of the output shaft (9) in response to flexure of the probe assembly being resisted. For example, organism tissue can be damaged by increasing the torque output to effect farther movement of the probe assembly (3) to overcome resistance to such movement by the organism tissue. The motor control apparatus (1) is self limiting to restrict farther bending of the articulating portion of the bendable probe assembly (3) when a predetermined, maximum limit to the force on the cable (4) is attained.

With reference to FIG. 2, each of the reversible drive mechanisms (7) further comprises, a secondary drive gear (11) coupled to the output shaft (9) of the articulation control motor (10) through another gear (11a) on the output shaft (9). The secondary drive gear (11) is affixed to a rotatable shaft (12) having an external, helical lead screw (14) that actuates a reciprocating shaft (14a). The helical lead screw (14) meshes with a follower in the form of a triangular projection on the shaft (14a). The shaft 14(a) subsequently reciprocates axially through the forward motor mounting block (23d). The shaft 14(a) extends along an open side of a channel (14b) facing the lead screw (14). The lead screw (14) meshes with the reciprocating shaft (14a) through the open side of the channel (14b). Rotation of the lead screw (14) drives the reciprocating shaft (14a) axially, forward and backward, by corresponding reversed rotation of the lead screw (14). Each reciprocating shaft (14a) is parallel with the parallel longitudinal axes of the articulation control cables (4, 4) to result in a slender housing (5) that is easily grasped by a human operator. The lead screw (14) on one side of the motor (10) has a right hand thread, and the lead screw (14) on the other side of the motor (10) has a left hand thread.

With reference to FIG. 2, the individual control cables (4, 4) connect to respective turnbuckles (18). Respective turnbuckles (18) connect the cables (4, 4) with the reciprocating shafts (14a) through an offsetting link. The individual control cables (4, 4) of the corresponding cable pair (2) extend from respective turnbuckles (18). A spring loaded, toggle link mechanism (21) connects to an axle (22). The axle (22) is rotatably mounted in a bearing block (23) that is attached to the housing (5). The bearing block (23) is attached to the housing (5) by being a turned up portion of a rigid frame (23a) that is attached to the housing (5). The frame (23a) provides an eyelet (23b) with respective channels through which the torque control cable (6) extends, and through which at least one articulation control cable (4) extends. The eyelet (23b) gathers the articulation control cables (4) and the torque control cable (6), FIG. 4, closely together in parallel with one another, with their longitudinal axes parallel with the lengthwise, respective motors (10, 10a) to provide a slender configuration. They additionally are in-line with the lengthwise respective motors (10, 10a) to provide a slender configuration. The motors (10, 10a) are mounted to a portion (23c) of the frame (23a) by being secured by motor mounts (23d) that are, in turn, mounted on the portion (23c) of the frame assembly (23a, 23c and 23e).

Each of the toggle links (21) comprises a spring loaded link (24) and a second link (25). An end of the second link (25) is pivotally mounted on the axle (22) rotatably mounted on the bearing block (23). Each end of the axle (22) is secured at the pivoting center of a hand operated, toggle lever (24') mounted on an exterior of the handle (5). Upon rotation of the lever (24') the toggle link mechanism (21) causes pivoting of each pulley (19) to apply tension on the corresponding cable pair (2), and couple the corresponding cable pair (2) to the drive mechanism (7). The lever (24') can be pivoted to an off position, for example, by pivoting in a reverse direction, so as to release tension on each corresponding cable pair (2), and to decouple each corresponding cable pair (2) from the drive mechanism (7). With reference to FIG. 2, the respective links (24, 25) are mounted on the frame (23a) in tandem alignment with the respective motors (10, 10a) and respective control line (6) and control cables (4, 4) to provide a slender configuration. The control line (6) and control cables (4, 4) pass through the link 25 that bends in close confinement around the control line (6) and control cables (4, 4), to provide a slender configuration.

With reference to FIG. 2, the control cables (4, 4) of a corresponding cable pair (2) extend from respective turnbuckles (18), and are turned around the cylindrical peripheries of respective tension adjusting pulleys (19) mounted for rotation on a link (25) of a link mechanism (21). The link (25) is connected by a rotatable shaft (22) to a pivoting lever (24'). The shaft is mounted to a bearing block (23). The control cables (4, 4) extend from the pulleys (19) and are turned around the cylindrical peripheries of respective idler pulleys (19a) that are mounted on spring loaded links (24) of the link mechanism (21). The links (24) extend through a mounting block (23'). The links (24) are spring loaded against the mounting block (23') to bias the pulleys (19a) and apply tension on the control cables (4, 4). The spring loaded links (24) are loaded with nominal spring pressure and apply nominal tension on the control cables (4, 4), preventing over-tensioning of the control lines (4, 4).

The nominal tension of the articulation control cables (4) is maintained by a spring loaded link (24) and a second link (25), for example, comprised of idler shafts (24) attached to pulleys through which the articulation control cables (4, 4) are routed. The articulation control cables (4) are also routed through similar pulleys which are affixed in the open ends of a pivotally mounted rotatable yoke of a link mechanism (21). This rotatable yoke is pivotally mounted on an axle (22). The axle (22) comprising this yoke assembly is rotatably mounted on the upturned portion of the mounting plate (23), shown in FIG. 2. The end of the axle (22) is secured at a pivoting axis of a hand operated, toggle lever (24') and mounted on an exterior of the housing (5). Upon rotation of the lever (24') in a clockwise direction, as shown in FIG. 2, the yoke assembly is moved to a vertical orientation, relative to the baseplates (23a, 23c and 23e), causing pivoting of each pulley (19) to apply tension on the corresponding cable pair (2), and couple the corresponding cable (4) to the drive mechanism (7). The lever (24') can be pivoted to an off position, for example, by pivoting in a clockwise direction, causing pivotal motion of each pulley (19) so as to release tension on each corresponding cable pair (2), and to decouple each corresponding cable pair (2) from the drive mechanism (7). With reference to FIG. 2, the torque control cable (6) and control cables (4, 4) pass through the central axis of the link 25 that comprises the toggle yoke (25) that bends in close confinement around the cables to provide a slender configuration.

With reference to FIG. 2, the control cables (4, 4) of a corresponding cable pair (2) extend from respective turnbuckles (18), and are turned around the cylindrical peripheries of respective tension adjusting pulleys (19) mounted for rotation on a link (25) of a link mechanism (21). The link (25) may comprise a yoke assembly (25), FIG. 2. The link (25) is connected by a rotatable shaft (22) to a pivoting lever (24'). The shaft (22) is mounted to a bearing block (23). For example, the pulleys (19) are mounted for rotation on the open ends of the rotatable yoke assembly (25). The link (25) is connected by a rotatable shaft (22) to a pivoting lever (24'). The shaft is mounted to a bearing block (23). The control cables (4, 4) extend from the pulleys (19) and are turned around the cylindrical peripheries of respective idler pulleys (19a) that are mounted on spring loaded links (24) of the link mechanism (21). The links (24) extend through a mounting block (23'). The links (24) are spring loaded against the mounting block (23') to bias the pulleys (19a) and apply tension on the control cables (4, 4). The spring loaded links (24) are loaded with nominal spring pressure and apply nominal tension on the control cables (4, 4), preventing over-tensioning of the control lines (4, 4).

With reference to FIG. 2, the lever (24') is pivotable counterclockwise to pivot the link (25), yoke assembly (25), and move the tension adjusting pulleys (19) farther from the pulleys (19a), and to apply tension on the cables (4, 4) to couple the corresponding cable pair (2) to the drive mechanism (1). Tension is relieved in the following manner. Pivoting the lever (24') clockwise moves the pulleys (19) closer to the pulleys (19a), and decouples the corresponding cable pair (2) from the drive mechanism (7).

In operation, the lever (24') can be manually pivoted by a human operator for two purposes. One purpose is to provide a redundant safety feature, or back-up safety feature, to decouple each cable pair (2) from the drive mechanism (7) as a safety feature. The second purpose is to decouple each cable pair (2) from the drive mechanism (7) to prevent accidental movement of the probe assembly, once the articulating end of the bendable probe assembly (3) has been manipulated to achieve a desired curved configuration.

With reference to FIG. 2, the control line (6) passes through an elongated hollow tube (9c) and connects to a drive shaft (39) of the torque control cable control motor (10a). The torque control cable (6) connects to the output shaft (9a) of the motor by an adjustable length link (9b). Rotation of the control cable (6) is accomplished by rotation of the reversible torque motor (10a). The reversible motor (10a) is a torque motor with a limited torque output to prevent farther rotation of the navigable probe assembly (3) in response to farther rotation of the probe assembly (3) being resisted by organism tissue, whereby damage to the organism tissue is avoided.

Figure 4:
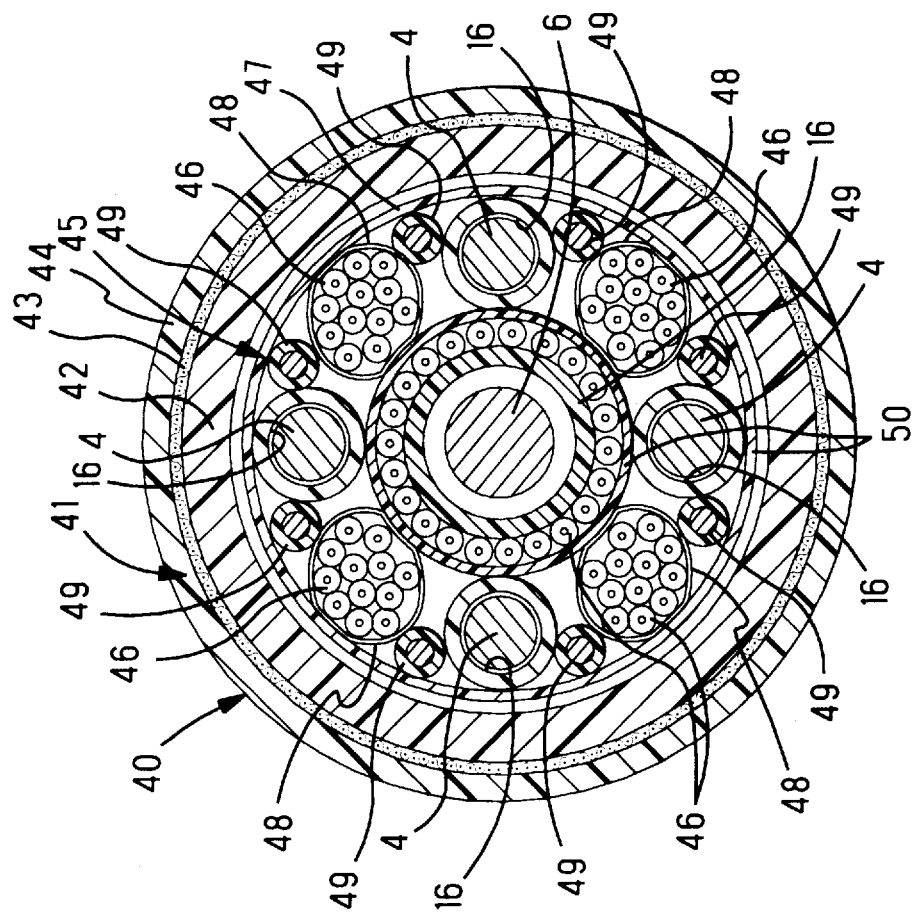
FIG. 4 is a cross section of the cable assembly as shown in FIG. 3.
Figure 2A:
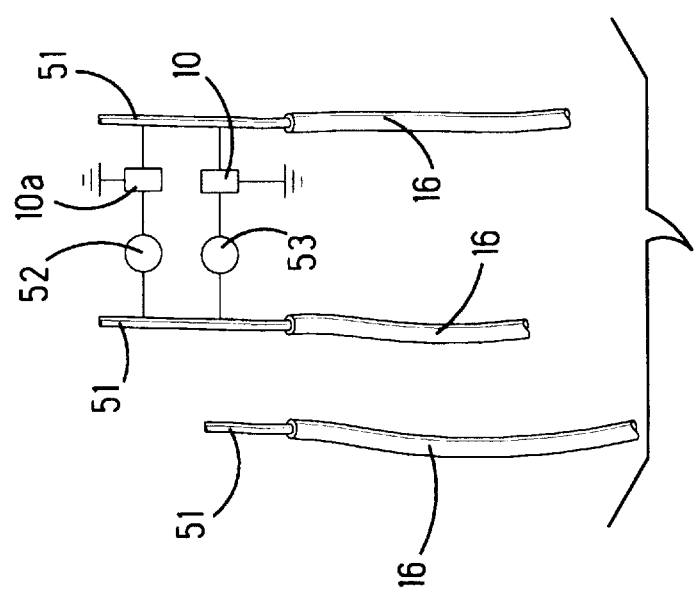

With reference to FIG. 4, the rotatable torque line (6) extends along a central axis of a signal transmitting cable assembly (40). An outer sheath (41) of the cable assembly (40) comprises a hollow metal tube armor (42), a tubular conducting braided sheath (43) surrounding the armor (42) and a continuous impervious layer (44) enclosing the braided sheath (43). The braided sheath (43) provides electrical shielding and laterally supports the armor (42). The armor is self supporting and provides an interior space within which an interior core (45) is inserted with ease. The impervious layer (44) is an outer layer of polymeric material that embedded in interstices of the braided sheath (43). The inner core (45) comprises the cable (6) concentric with and rotatably received within, and encircled by, a corresponding sheath (16). The core (45) further comprises each articulation control line (4) slidable within a corresponding sheath (16).

The core (45) further comprises, axially extending coaxial cables (46) extending axially in respective spaces separating the sheaths (16) from one another.

These coaxial cables (46) are signal transmitting conductors that transmit phased or synchronous signals from a known ultrasound imaging transducer, not shown, for conversion in a known manner to an ultrasound image of an area being probed by the probe assembly (3). The core (45) further comprises a sleeve (47) of polymeric material that readily slides within the interior of the armor (42). Tension applied on alternate ones of the cables (4) causes such cable (4) to slidably traverse within a corresponding sheath (16) that provides low friction resistance to movement, as well as abrasion protection for the signal transmitting conductors that comprise the coaxial cables (46). Each cable (4) is connected to a bendable portion of the probe assembly (3), which causes the probe assembly to bend or flex when pulled by a cable (4). The coaxial cables (46) are closely packed in the spaces within the sheath (45) to maintain the spacing of the articulation control lines (4) over the passage of time, such that the same amount of tension applied to the cables (4) results in the same relative movement of the bendable probe assembly (3). The control lines (4) and the corresponding sheaths (16) are forced by the coaxial cables (46) radially outward toward the interior of the inner core (45). Each control line (4) is radially spaced by a relatively long moment arm from the central axis of the cable assembly (40) to produce torque sufficient bend the probe assembly (3) with ease by tension being applied to the control line (4). The encircling armor (42) resists damage by compression, for example, by reflexive biting by a medical patient.

The multiple coaxial cables (46) are grouped in longitudinal bundles (48) and laterally support the sheaths (16) along orthogonal axes centered on the central axis of the cable assembly (40). Each bundle (48) is wrapped by polytetrafluoroethelyene tape (50) to provide a slippery surface to insert the bundle (48) along the longitudinal space along the interior of the inner core (45). Optional insulated wires (49) can be provided in the spaces among the bundles (48). The sleeve (15) comprises helical wraps of polytetrafluoroethylene tape (50) that will readily slide within the outer sheath (41). Additional helical wraps of the tape (50) concentrically encircle the corresponding sheath (16) that encircles the cable (6), making the bundles (48) and the insulated wires (49) readily slidable to reduce friction when the cable assembly (1) undergoes flexure.

As shown in FIG. 4a, known electrical insulated wires (51) provide a familiar combination of two insulated wires for supplying electrical power over two wires, in combination with a third wire for supplying a ground connection. The third, ground connection, wire can be insulated, as shown, or uninsulated. Two of the wires (51) connect the primary motor (10) and the motor (10a) with respective, reversible, on-off switches (52, 53). The switches (52, 53) are described, along with further details of the apparatus (1), in U.S. patent application Ser. No. 08/921411, incorporated herein by reference. A third insulated wire (51) provides a separate ground or earth electrical connection for the chassis of each motor (10, 10a). The motors (10, 10a) are constructed in a known manner as having electrical connection structures adapted for easily connecting the wires (51).

With reference to FIG. 1, the insulated wires (51) are constructed for combination with the cable assembly (40). The With reference to FIG. 3, the cable assembly (40) is constructed for connecting to the probe assembly (3), as well as being connected to parts of the apparatus (1) that are contained by the housing (5). With reference to FIG. 1, the reciprocating articulation control cables (4) and the rotating control cable (6) extend along corresponding portions of the sheaths (16) in a first portion (54) of the cable assembly (40), FIG. 1. Portions of the cables (4 and 6) and portions of the sheaths (16) emerge outwardly from a remainder of the cable assembly (40) by first being exposed at spaced apart cut openings (55, 56) in the sheath (41) of the cable assembly (40). Then the corresponding sheaths (16) that are exposed at the cut opening (55) are severed adjacent to the cut opening (55). Substantial lengths of the cables (4 and 6) are drawn out from the severed corresponding sheaths (16) to expose substantial lengths of the cables (4 and 6) that project from the cut opening (55) in a first portion of the cable assembly (40). Then these exposed lengths of the cables (4 and 6) are themselves severed at sufficient lengths to allow the cables (4 and 6) to project from the cut opening (55) to be connected, respectively, to the corresponding reversible drive mechanisms (7) and the reversible motor (10a). With the cables (4 and 6) having been removed from the severed portions of the corresponding sheaths (16), said portions of the sheaths (16) are pulled out from the cut opening (56) in a second portion (57) of the sheath (41) of the cable assembly (40).

With reference to FIG. 1, the insulated wires (51) are fed into and along the severed portions of the sheaths (16) that extend along the second portion (57) of the cable assembly. First ends of the insulated wires (51) project from the ends of the severed portions of the sheaths (16), and connect to the motors (10, 10a), FIG. 3.

As shown in FIG. 1, the insulated wires (51) are within the second portion (57) of the cable assembly (40). The insulated wires (51) are connected to a known electrical connector (58), for example, as described in U.S. Pat. No. 3,901,574, incorporated herein by reference. The signal transmitting conductors (50) of the cable assembly are also connected to the electrical connector (58) that terminates the cable assembly (40). With reference to FIG. 3, the cable assembly (40) extends within the housing (5), with the portion (54) projecting through a sealed cable opening (59) formed by two halves of the housing (5), and with the portion (57) projecting through a sealed cable opening (60) formed by two halves of the housing (5).

Although preferred embodiments have been described, other embodiments and modifications of the invention are intended to be covered by the spirit and scope of the appended claims.

What is claimed is:

1. An ultrasound imaging apparatus, comprising: a rotating torque control cable for rotating an ultrasound transducer on a probe assembly, at least one articulation control cable to flex the probe assembly by reciprocating movement of said control cable, each said articulation control cable and said torque control cable being received along a corresponding sheath contained in a first portion of a signal transmitting cable assembly, each said articulation control cable and said torque control cable having respective portions being separate from a remainder portion of said cable assembly, a first reversible motor having an output shaft connected to said portion of said torque control cable that is separate from said remainder portion of said cable assembly, at least a second reversible motor connected to a reversible drive mechanism, said mechanism being coupled to said portion of each said articulation control cable that is separate from said remainder portion of said cable assembly, and insulated wires connected to said reversible motors to connect said reversible motors to a source of electrical power, said insulated wires extending through said corresponding sheaths in said remainder portion of said cable assembly.

2. An ultrasound imaging probe assembly comprising: a rotating torque control line to rotate an ultrasound transducer on the probe assembly, at least one pair of articulation control cables to flex the probe assembly by equal and opposite simultaneous reciprocating movement of the articulation control cables, said articulation control cables being reciprocatingly received along corresponding sheaths, a flexible and limp cable assembly containing said sheaths, portions of said articulation control cables projecting outwardly of said cable assembly and being connected to a reversible drive mechanism.

3. A navigable probe assembly comprising: a bendable portion of the probe assembly, a signal transmitting cable assembly having multiple signal carrying conductors extending to an imaging transducer on the probe assembly, reciprocating articulation control cables attached to the probe assembly, a reversible drive mechanism having a first reversible motor for reciprocating the reciprocating cables, a rotating torque control cable connected to the transducer, a second reversible motor for rotating the rotating cable, first portions of corresponding sheaths extending within a first portion of said cable assembly, a projecting portion of each said reciprocating cable projecting outward from said first portion of a corresponding sheath, each said reciprocating cable projecting outward from said first portion of said cable assembly and being connected to said drive mechanism, a projecting portion of said rotating cable projecting outward from said first portion of a corresponding sheath and being connected to an output shaft of said second reversible motor, second portions of said corresponding sheaths extending along a second portion of said signal transmitting cable and emerging from said second portion, insulated wires extending through said second portions of said corresponding sheaths, said insulated wires electrically connecting with said reversible motors and electrically connecting said reversible motors with an electrical connector.

4. A navigable probe assembly as recited in claim 3, and further comprising, a housing enclosing said drive mechanism and said reversible motors, said cable assembly extending through said housing, said first portion of said cable assembly emerging from a first end of said housing, and said second portion of said cable assembly emerging from a second portion of said housing.

5. A navigable probe assembly comprising: a rotating torque control cable for rotating an ultrasound imaging transducer, reciprocating articulation control cables for bending a portion of the probe assembly, and a cable assembly having signal transmitting cables connected to the transducer, first portions of corresponding sheaths from which project corresponding portions of said cables, said first portions of corresponding sheaths extending in a first portion of said cable assembly, second portions of said corresponding sheaths extending in a second portion of said cable assembly, insulated wires extending along said second portions of said corresponding sheaths, the insulated wires being connected to said motors, and to an electrical connector.

6. A navigable probe assembly as recited in claim 5, and further comprising: a housing containing said motors and said reversible drive mechanism, said first portion of said cable assembly extending from a first portion of said housing, and said second portion of said cable assembly extending from a second portion of said housing.

* * * * *